US012037267B2

(12) United States Patent
Li et al.

(10) Patent No.: US 12,037,267 B2
(45) Date of Patent: Jul. 16, 2024

(54) UV LED FAUCET FLOW CELL

(71) Applicant: A. O. SMITH CORPORATION, Milwaukee, WI (US)

(72) Inventors: Chen Li, Menomonee Falls, WI (US); Michael John Verhaalen, Sussex, WI (US); Botao Peng, Waterloo (CA)

(73) Assignee: A.O. Smith Corporation, Milwaukee, WI (US)

( * ) Notice: Subject to any disclaimer, the term of this patent is extended or adjusted under 35 U.S.C. 154(b) by 450 days.

(21) Appl. No.: 17/435,983

(22) PCT Filed: Apr. 30, 2020

(86) PCT No.: PCT/US2020/030763
§ 371 (c)(1),
(2) Date: Sep. 2, 2021

(87) PCT Pub. No.: WO2020/223506
PCT Pub. Date: Nov. 5, 2020

(65) Prior Publication Data
US 2022/0153611 A1 May 19, 2022

Related U.S. Application Data

(60) Provisional application No. 62/841,935, filed on May 2, 2019.

(51) Int. Cl.
*C02F 1/32* (2023.01)
*A61L 2/10* (2006.01)
*A61L 2/26* (2006.01)

(52) U.S. Cl.
CPC .............. *C02F 1/325* (2013.01); *A61L 2/10* (2013.01); *A61L 2/26* (2013.01); *A61L 2202/11* (2013.01);
(Continued)

(58) Field of Classification Search
CPC .............. C02F 1/325; C02F 2201/3222; C02F 2201/3228; C02F 2303/04; C02F 2307/06;
(Continued)

(56) References Cited

U.S. PATENT DOCUMENTS 7,049,615 B1  5/2006  Browne
7,270,748 B1 * 9/2007  Lieggi ................... C02F 1/325
                                                                   250/435

(Continued)

FOREIGN PATENT DOCUMENTS

CN     103945712 A    7/2014
WO     2019055348 A1  3/2019

OTHER PUBLICATIONS

International Preliminary Report on Patentability for Application No. PCT/US2020/030763 dated Nov. 2, 2021 (8 pages).
(Continued)

*Primary Examiner* — David A Vanore
(74) *Attorney, Agent, or Firm* — Michael Best & Friedrich LLP

(57) ABSTRACT

A water dispensing unit adapted for communication with a water supply includes a main body including a first end, a second end opposite the first end, a first axis extending through the first and second ends, and a second axis extending perpendicular to the first axis. The water dispensing unit additionally includes an inlet configured to receive water from the water supply, an outlet configured to dispense water, wherein the outlet extends along an outlet axis, an inner wall including a reflective liner, and a light emitting diode positioned within the main body. The outlet axis is oriented at an angle relative to the second axis to direct water from the water supply toward the light emitting diode before exiting through the outlet.

19 Claims, 3 Drawing Sheets

(52) U.S. Cl.
CPC ............ *C02F 2201/3222* (2013.01); *C02F 2201/3228* (2013.01); *C02F 2303/04* (2013.01); *C02F 2307/06* (2013.01); *C02F 2307/10* (2013.01)

(58) Field of Classification Search
CPC .......... C02F 2307/10; A61L 2/10; A61L 2/26; A61L 2202/11
See application file for complete search history.

(56) References Cited

U.S. PATENT DOCUMENTS

| | | | |
|---|---|---|---|
| 8,226,831 B2 | 7/2012 | Maiden | |
| 9,260,323 B2* | 2/2016 | Boodaghians | C02F 1/325 |
| 9,498,550 B2 | 11/2016 | Kneissl et al. | |
| 9,540,252 B1* | 1/2017 | Collins | A61L 2/10 |
| 9,592,102 B2 | 3/2017 | Knight et al. | |
| 9,617,171 B2* | 4/2017 | Rajagopalan | C02F 1/325 |
| 9,745,209 B2 | 8/2017 | Chen et al. | |
| 9,802,840 B2 | 10/2017 | Shturm et al. | |
| 9,855,363 B2 | 1/2018 | Stokes et al. | |
| 9,938,165 B2 | 4/2018 | Taghipour | |
| 10,294,124 B2* | 5/2019 | Khan | C02F 1/325 |
| 2005/0077732 A1* | 4/2005 | Baarman | F03B 1/00 290/54 |
| 2007/0045197 A1 | 3/2007 | Ogut et al. | |
| 2010/0314551 A1 | 12/2010 | Bettles et al. | |
| 2012/0051977 A1* | 3/2012 | Boodaghians | C02F 1/325 422/186.3 |
| 2015/0008167 A1 | 1/2015 | Shturm et al. | |
| 2015/0114912 A1 | 4/2015 | Taghipour | |
| 2015/0144575 A1 | 5/2015 | Hawkins, II | |
| 2016/0046508 A1 | 2/2016 | Orita | |
| 2016/0355412 A1 | 12/2016 | Collins et al. | |
| 2018/0051447 A1 | 2/2018 | Hills et al. | |
| 2018/0354814 A1 | 12/2018 | Tymchuk et al. | |

OTHER PUBLICATIONS

Chinese Patent Office Action for Application No. 202080032919.2 dated Sep. 16, 2023 (26 pages including English translation).

* cited by examiner

UV LED FAUCET FLOW CELL

CROSS-REFERENCE TO RELATED APPLICATIONS

This application claims priority to U.S. Provisional Patent Application No. 62/841,935, filed on May 2, 2019, the entire contents of which are incorporated by reference herein.

FIELD OF THE INVENTION

The present invention relates to faucet flow cells and, more particularly, to faucet flow cells operable to disinfect water at point-of-use.

BACKGROUND

Microbiological secondary contamination after reverse osmosis (RO) treatment is an industry-side problem. UV-LEDs, because of their small size, provide a new method for point-of-dispense disinfection. Often times, faucet flow cells may be constructed with reflective materials to increase flux intensity. These materials may include PTFE, aluminum, stainless steel, etc., and all have various advantages and disadvantages. For example, PTFE includes high reflectivity but is expensive and difficult to form on specific surfaces. Alternatively, metals are less expensive than PTFE, but produce lower reflectivity values and may not be in direct contact with potable water.

The geometry of a purification reactor may allow microorganisms to dwell within a reactor long enough to increase UV dosage. Some methods to eliminate such microorganisms include extending the length of the reactor, thereby increasing the mean UV dosage. However, since LEDs are point light sources, UV intensity ultimately drops significantly along a longitudinal axis of the reactor. Additionally, oversized reactors pose a risk of decreasing minimum dosage, which determines the microorganism reduction rate as the mean dosage increases.

SUMMARY

In one aspect, the invention provides a water dispensing unit adapted for communication with a water supply, including a main body including a first end, a second end opposite the first end, a first axis extending through the first and second ends, and a second axis extending perpendicular to the first axis, an inlet configured to receive water from the water supply, an outlet configured to dispense water, wherein the outlet extends along an outlet axis, an inner wall including a reflective liner, and a light emitting diode positioned within the main body, wherein the outlet axis is oriented at an angle relative to the second axis to direct water from the water supply toward the light emitting diode before exiting through the outlet In another aspect, the invention provides a water dispensing unit adapted for communication with a water supply, including a main body including a first end, a second end opposite the first end, and a longitudinal axis extending through the first and second ends, an inlet configured to receive water from the water supply, an outlet configured to dispense water, a liner positioned along an inner surface of the main body, wherein the liner includes a first reflectivity value, and an end wall positioned on the first end of the main body, wherein the end wall includes a light window and a light emitting diode, and wherein the end wall includes a second reflectivity value greater than the first reflectivity value.

In another aspect, the invention provides a water dispensing unit adapted for communication with a water supply, including a main body including a first end, a second end opposite the first end, a first axis extending through the first and second ends, and a second axis extending perpendicular to the first axis, an inlet configured to receive water from the water supply, wherein the inlet extends along an inlet axis, an outlet configured to dispense water, wherein the outlet extends along an outlet axis, a liner positioned along an inner surface of the main body, wherein the liner includes a first reflectivity value, and an end wall positioned on one of the first end and the second end of the main body, wherein the end wall includes a light window and a light emitting diode, wherein the end wall includes a second reflectivity value greater than the first reflectivity value, wherein one of the inlet axis and the outlet axis is oriented at an angle relative to the second axis to direct water from the water supply toward the light emitting diode.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
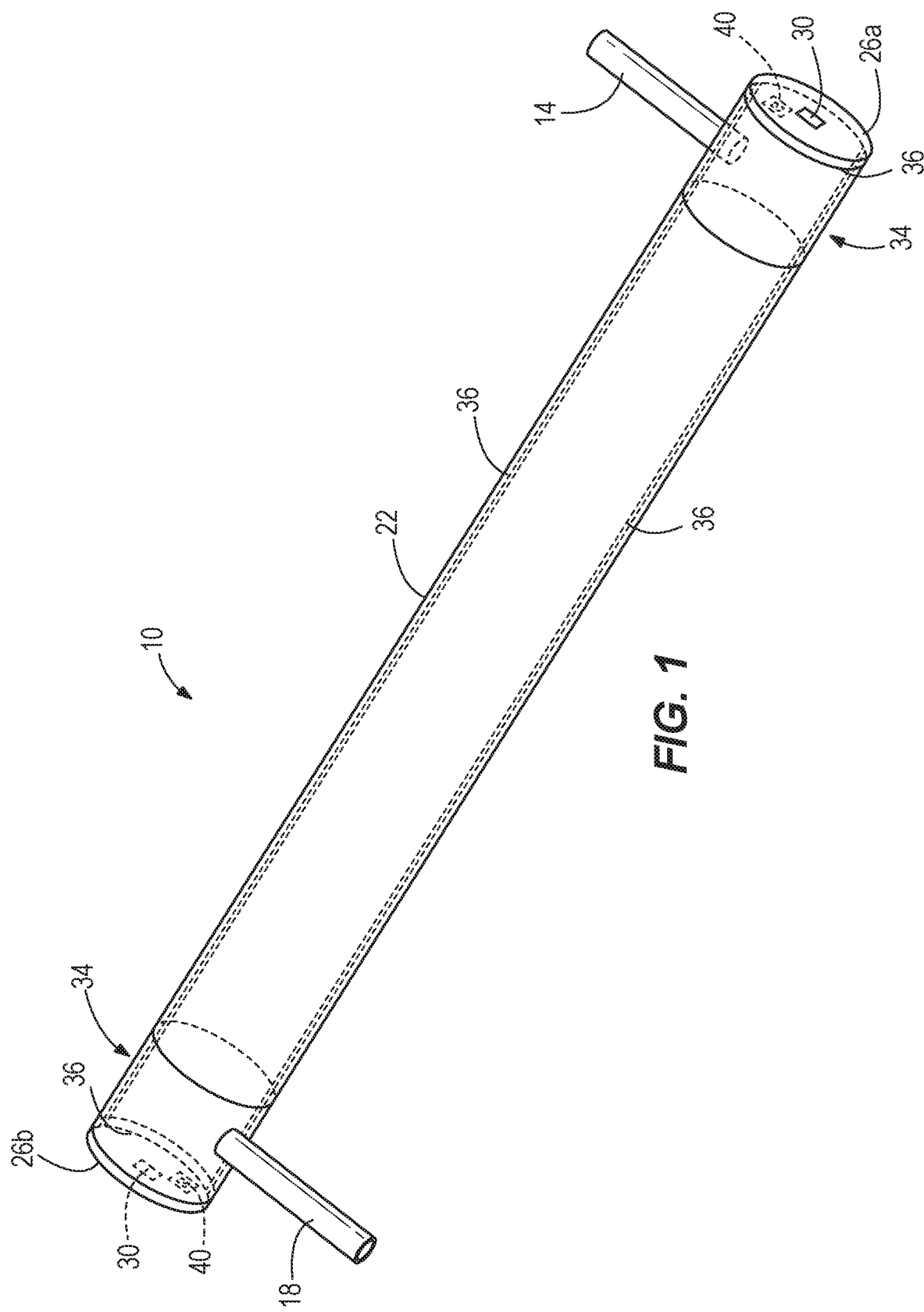
FIG. 1 is a perspective view of a faucet flow cell embodying the invention.
Figure 2:
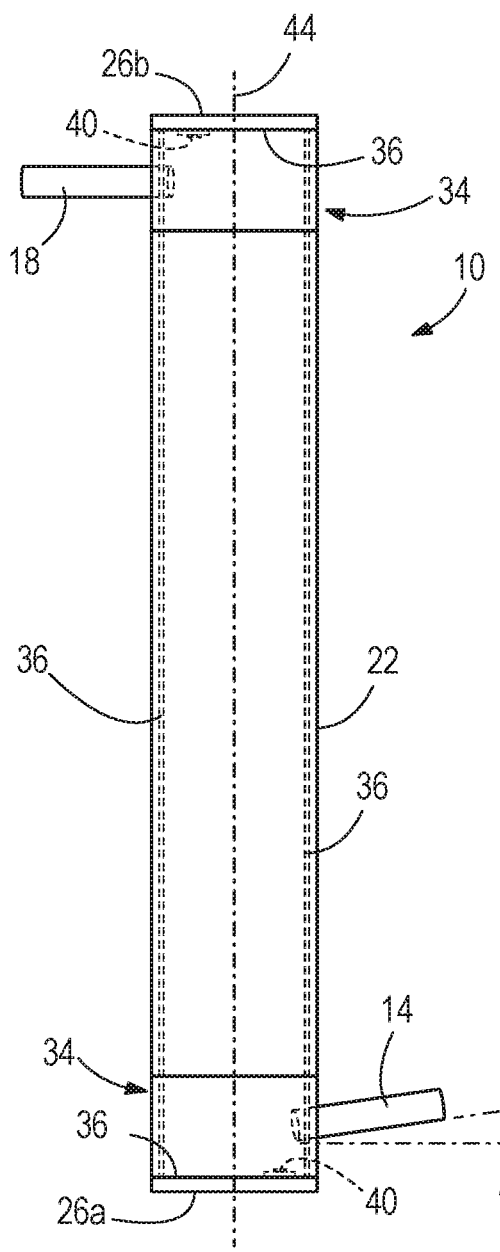
FIG. 2 is a side view of the faucet flow cell of FIG. 1, including an inlet of the faucet flow cell positioned at an angle.
Figure 3:
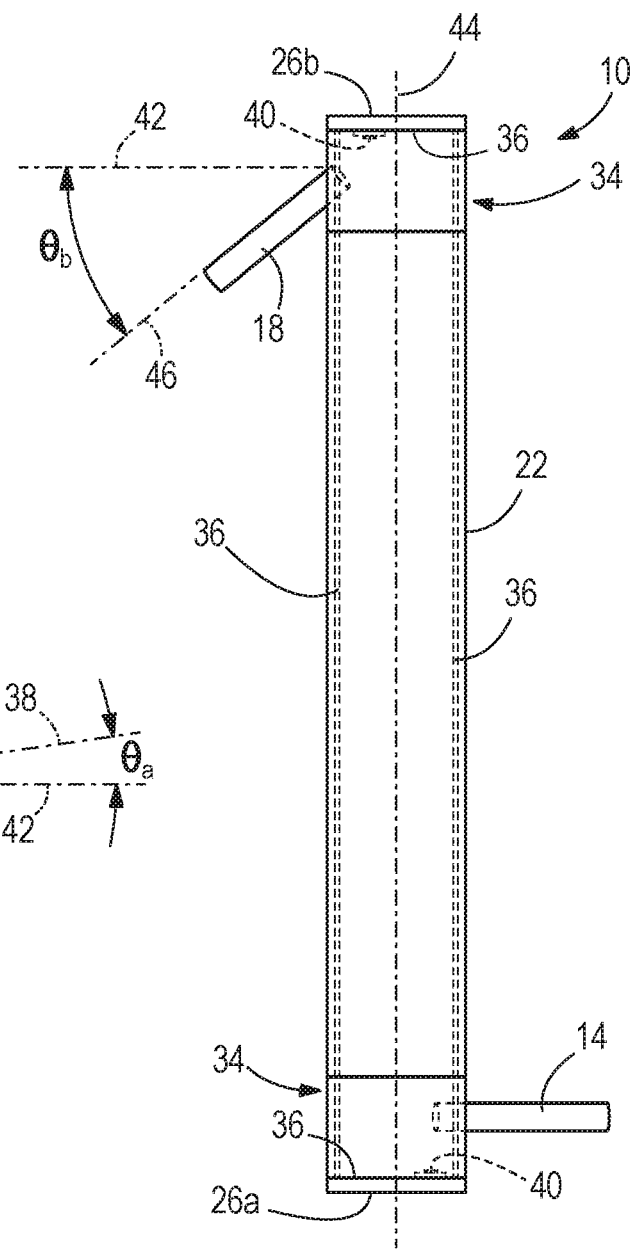
FIG. 3 is another side view of the faucet flow cell of FIG. 1, including an outlet of the faucet flow cell positioned at an angle.

FIGS. 1-3 illustrate a faucet flow cell 10 embodying the invention. The faucet flow cell 10 includes an inlet, or inlet tube, 14 and an outlet, or outlet tube, 18. The faucet flow cell 10 receives water from a water supply through the inlet 14 and dispenses the water through the outlet 18. The faucet flow cell 10 additionally includes a sidewall 22, a first end wall 26a, a second end wall 26b, and at least one light window 30.

The faucet flow cell 10 may more generally be referred to as a water dispensing unit. The water supply delivers water to the inlet 14 either directly from a municipal supply or from a filtration unit such as a reverse osmosis system or carbon filter. The water supply may therefore be characterized as downstream from the filtration unit, and/or a municipal supply, and upstream of the inlet 14. A flow of water from the water supply into the inlet 14 is defined as being a downstream water flow. An upstream direction is defined as opposite the downstream water flow. More specifically, the water supply may be characterized as water received from a municipal water supply, optionally purified or treated or filtered, and contained within a space directly upstream of the faucet flow cell 10.

With reference to FIG. 1, the faucet flow cell 10 is cylindrical. More specifically, the sidewall 22 is substantially rounded and the first and second end walls 26a, 26b are flat. The sidewall 22 extends between the first and second end walls 26a, 26b. In alternative embodiments, the faucet flow cell 10 may include different shapes (e.g., conical, rectangular, etc.), thereby providing a flat sidewall 22 and/or rounded end walls 26a, 26b. The first end wall 26a is positioned adjacent the inlet 14, and the second end wall 26b is positioned adjacent the outlet 18. In alternative embodiments, the inlet 14 and outlet 18 may be positioned at alternative locations on the faucet flow cell 10.

The sidewall 22 and the end walls 26a, 26b are constructed of reflective materials. More specifically, the flow cell 10 may be constructed from plastics, metals (e.g., stainless steel), zinc, and/or copper. A porous PTFE reflective film, or liner, 36 such as a reflective film available from Porex, Inc., may be secured to an inner surface of the sidewall 22 and end walls 26a, 26b. Specifically, the porous PTFE reflective film 36 may be glued to the walls 22, 26a, 26b via a primer and adhesive. In some embodiments, the reflective liner 36 is only secured to the end walls 26a, 26b. In some embodiments, the PTFE film 36 includes a preformed shape, which aligns with the shape of the sidewall 22 and end walls 26a, 26b.

In alternative embodiments, a guiding tool may be placed within the faucet flow cell 10 adjacent the end walls 26a, 26b. In such instances, the porous PTFE reflective film 36 may be inserted into the faucet flow cell 10 via the guiding tool and covers the length of the flow cell 10. In further embodiments, PTFE 36 may be pressed and sintered onto the internal surface of the end walls 26a, 26b. In another alternative embodiment, the PTFE reflective film 36 may be backed with polypropylene, allowing the reflective film 36 to be welded to surfaces. In still further embodiments, an inner transmissive wall may be formed by molding quartz and/or PFA fluoropolymer to the same shape of the flow cell 10. PTFE heat-shrinking is then used to shrink the transmissive layer onto the side wall 22 and end walls 26a, 26b.

In the illustrated embodiments, the flow cell 10 includes a diameter of approximately 22.5 mm-45.0 mm. Furthermore, the sidewall 22 includes a length less than or equal to 20 times the diameter (e.g., 450.0 mm-900 mm). The reflective film 36 on the end walls 26a, 26b is thicker than the reflective film 36 on the sidewall 22. More specifically, the reflective film 36 on the end walls 26a, 26b includes a thickness of 0.25 mm-1.5 mm and the reflective film 36 on the sidewall 22 includes a thickness of 0.05 mm-1.0 mm. Although the side wall 22 includes greater surface area than the end walls 26a, 26b, the end walls 26a, 26b have more impact on increasing UV intensity than the sidewall 22 because reflectivity is determined by the thickness of the reflective film 36. Therefore, the sidewall 22 and the end walls 26a, 26b include different amounts of reflectivity. More specifically, the ends walls 26a, 26b include a level of reflectivity greater than or equal to the reflectivity of the sidewall 22. For example, reflectivity of 0.25 mm, 0.75 mm, and 1.5 mm POREX® material are 85%, 95%, and 98% respectively.

Figure 4:
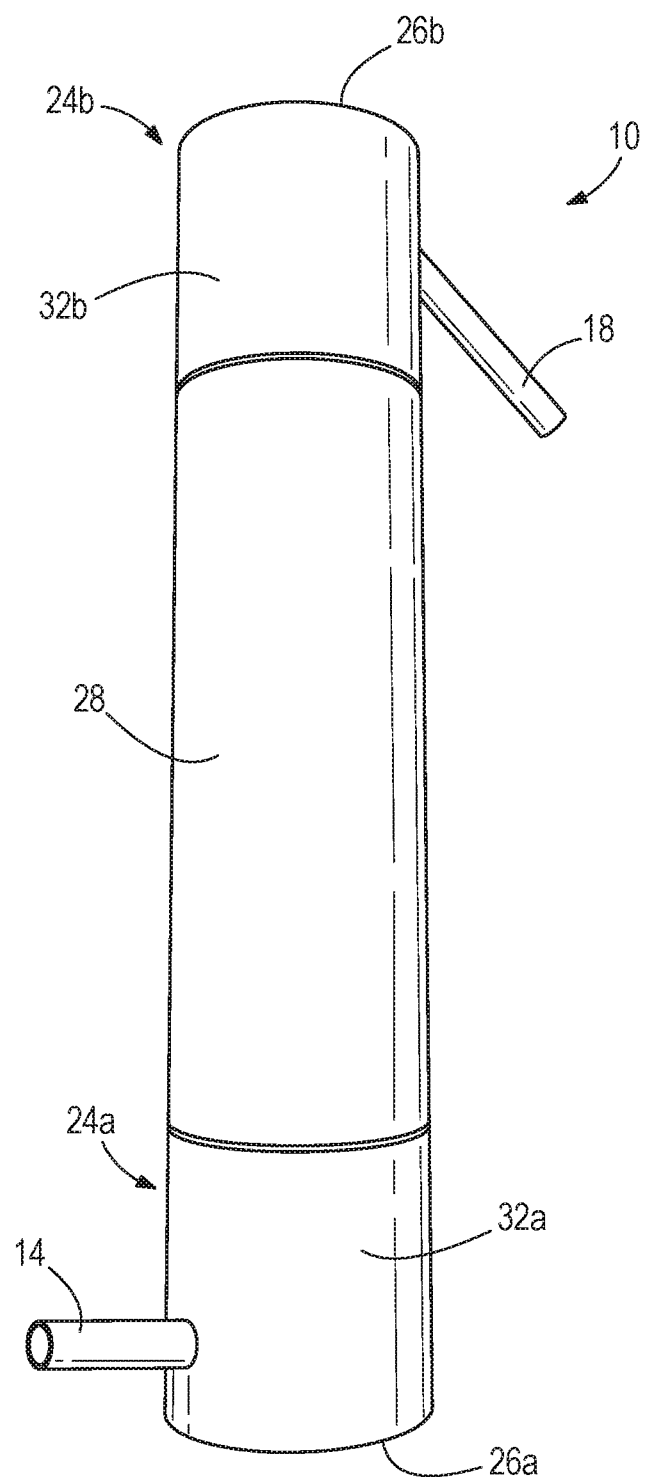
FIG. 4 is a side view of an alternative faucet flow cell.

In some embodiments (FIG. 4), the faucet flow cell 10 may be constructed of two cylindrical end portions, or end caps, 24a, 24b and a main body 28. In such embodiments, the end portions 24a, 24b are cylindrical and include a sidewall 32a, 32b in addition to the end walls 26a, 26b. More specifically, the sidewall 32 is substantially shorter than the sidewalls 22 illustrated in FIGS. 1-3. The sidewall 32 includes a length shorter than a length of the main body 28. The end portions 24a, 24b may be secured to the main body 28 via a welding process or alternative fastening method (e.g., via fasteners). The inlet tube 14 and outlet tube 18 may be positioned on the sidewall 32a, 32b of the end portions 24a, 24b. In such instances, a reflective value of inner walls of the end portions 24a, 24b is higher than a reflective value of the main body 28. In the illustrated embodiment, the reflective film may only secured to the end portions 24a, 24b.

With reference to FIGS. 2-3, at least one light window 30 may be placed on the end walls 26a, 26b. In the illustrated embodiments, the first end wall 26a and second end wall 26b each include a light window 30. In alternative embodiments, the faucet flow cell 10 may include fewer or greater than two light windows 30. The light windows 30 are composed of quartz, FEP, and/or PFA. The light windows 30 are sized based on UV-LED chip size. Specifically, the light windows 30 do not exceed 10 mm in diameter. However, in alternative embodiments, the light windows 30 may include alternative sizes.

The end wall 26 of the faucet flow cell 10 additionally includes two UV light emitting diodes (LEDs) 40. The UV LEDs 40 are mounted on the end wall 26 substantially opposite from each other. Specifically, the UV LEDs 40 form a high UV intensity zone 34 capable of irradiating microbes and other bacteria found within the water from the water supply. At least one of the UV LEDs 40 is placed on the end wall 26 adjacent the outlet 18 to reflect light in the region surrounding the outlet 18. More specifically, the UV LED 40 and reflective sidewall 22 radiate such that water exiting the flow cell 10 is irradiated of microbes. In alternative embodiments, an additional UV LED may be positioned within the outlet 18. In such instances, the outlet UV LED may contain lower power and be controlled separately from the UV LEDs 40 on the end wall 26 in order to separately disinfect the outlet 18. Specifically, the outlet UV LED may be turned on every 1-8 hours for 1-120 seconds.

In some embodiments, the faucet flow cell 10 includes one light window 30 and one UV LED 40. In such instances, the light window 30 and the UV LED 40 are positioned on one of the end walls 26a, 26b. More specifically, the light window 30 and the UV LED 40 are both positioned on the first end wall 26a or the second end wall 26b. The end wall 26a, 26b including the light window 30 and the UV LED 40 includes a level of reflectivity greater than the reflectivity of the end wall 26a, 26b without the light window 30 and the UV LED 40, and the end wall 26a, 26b without the light window and the UV LED 49 includes a level of reflectivity greater than the sidewall 22. In some embodiments, the end wall 26a, 26b including the light window 30 and the UV LED 40 includes a level of reflectivity less than the reflectivity of the sidewall 22. Furthermore, in some embodiments, the end walls 26a, 26b include the same level of reflectivity.

The UV LEDs 40 described herein are 265 nm and composed of a pure AlN substrate. However, in alternative embodiments, LEDs with different wavelengths may be used (e.g., 275 nm, 280 nm, 285 nm, etc.). In alternative embodiments, the faucet flow cell 10 may include fewer or greater than two UV LEDs. In still further embodiments, the faucet flow cell 10 may include different types of LEDs.

With reference to FIG. 2, the inlet tube 14 is positioned adjacent the first end wall 26a. An inlet axis 38 extends along the length of the inlet tube 14. The inlet axis 38 is substantially angled toward the center of one of the UV LEDs 40, forming a first impinging jet on a lens surface of one of the UV LEDs 40. Specifically, a first, or inlet, jet angle $\theta_a$ is defined as the angle between the inlet tube axis 38 and the plane of the first end wall 26a which is represented by a horizontal axis 42 (i.e., an axis perpendicular to a longitudinal axis 44 of the flow cell 10) and is approximately 5-20 degrees. In alternative embodiments, the first jet angle $\theta_a$ may be within different ranges. The first impinging jet directs water from the water source to the lens surface of one of the UV LEDs 40 and the high UV intensity zone 34, thereby irradiating any microbes found in the water source.

With reference to FIG. 3, the outlet tube 18 acts as a waterspout and is positioned adjacent the second end wall 26b. An outlet axis 46 extends along the length of the outlet tube 18. The outlet axis 46 is substantially angled toward the center of one of the UV LEDs 40 to form a second impinging jet on a lens surface of one of the UV LEDs 40. A second, or outlet, jet angle $\theta_b$ is defined as the angle between the outlet tube axis 46 and the plane of the second end wall 26b which is represented by the horizontal axis 42 and is approximately 0-45 degrees. In alternative embodiments, the second jet angle $\theta_b$ may be within different ranges. The second jet angle $\theta_b$ allows more UV radiation to reach the outlet tube, or faucet tip, 18. For example, a 45-degree jet angle will increase the UV intensity at the spout tip by 73%.

Operation and effectiveness of the faucet flow cell 10 to irradiate microbes is dependent on inlet jet angle $\theta_a$, the diameter of the ends walls 26a, 26b, and the length of the flow cell 10. During operation of the flow cell 10, microorganisms are continuously directed to the second end wall 26b, where they are irradiated. However, altering the parameters of the faucet flow cell 10 impact its effectiveness. For example, increasing the diameter of the flow cell 10 past a certain value (e.g., 45.0 mm) may reduce mixing effects and irradiation. As shown in the Table 1 below, altering the inlet jet angle $\theta_a$ while maintaining a constant flow cell diameter (e.g., 28.5 mm) and length (185 mm) impacts the UV dosage within the flow cell 10. Specifically, the results below were conducted using a 2 L/min flow rate with two 30 mW LEDs.

TABLE 1

Impact of Inlet Jet Angle on UV Dosage

| Inlet Jet Angle (degrees) | 0 | 10 | 20 |
|---|---|---|---|
| Mean Dosage (mJ/cm$^2$) | 33.59 | 33.42 | 31.22 |
| Maximum Dosage (mJ/cm$^2$) | 661.4 | 699.1 | 414.5 |
| Minimum Dosage (mJ/cm$^2$) | 8.703 | 11.41 | 10.57 |
| Standard Deviation (mJ/cm$^2$) | 30.79 | 29.18 | 23.08 |

As illustrated in Table 1, the highest mean UV dosage (e.g., 33.59 mJ/cm$^2$) occurs with an inlet jet angle $\theta_a$ of approximately 0°. Furthermore, highest maximum dosage of UV occurs at an inlet jet angle $\theta_a$ of 10°, with approximately 699.1 mJ/cm$^2$, and the lowest minimum UV dosage occurs at an inlet jet angle $\theta_a$ of 0°, with approximately 8.703 mJ/cm$^2$. The highest standard deviation occurs at an inlet jet angle $\theta_a$ of 0°, with a standard deviation of 30.79.

With reference to Table 2 below, altering the diameter of the flow cell 10 while maintaining a constant inlet jet angle $\theta_a$ (e.g., 10°) and length (185 mm) impacts the UV dosage within the flow cell 10.

TABLE 2

Impact of Flow Cell Diameter on UV Dosage

| Diameter (mm) | 19.00 | 28.50 | 38.00 | 47.50 |
|---|---|---|---|---|
| Mean Dosage (mJ/cm$^2$) | 23.43 | 33.42 | 38.51 | 44.75 |
| Maximum Dosage (mJ/cm$^2$) | 318.3 | 699.1 | 396.1 | 412.0 |
| Minimum Dosage (mJ/cm$^2$) | 6.941 | 11.41 | 11.79 | 10.87 |
| Standard Deviation (mJ/cm$^2$) | 21.95 | 29.18 | 24.02 | 27.41 |

As illustrated in Table 2, the highest mean UV dosage (e.g., 44.75 mJ/cm$^2$) occurs with a diameter of approximately 47.50 mm. Furthermore, highest maximum dosage of UV occurs at a diameter of 28.50 mm, with approximately 699.1 mJ/cm$^2$, and the lowest minimum UV dosage occurs at a diameter of 19.00 mm, with approximately 6.971 mJ/cm$^2$. The highest standard deviation occurs at a diameter of 47.50 mm, with a standard deviation of 27.41.

With reference to Table 3 below, altering the length of the flow cell 10 while maintaining a constant inlet jet angle $\theta_a$ (e.g., 10°) and flow cell diameter (28.5 mm) impacts the UV dosage within the flow cell 10.

TABLE 3

Impact of Flow Cell Length on UV Dosage

| Length (mm) | 92.50 | 185.0 | 277.5 | 370.0 |
|---|---|---|---|---|
| Mean Dosage (mJ/cm$^2$) | 29.40 | 33.42 | 32.04 | 31.78 |
| Maximum Dosage (mJ/cm$^2$) | 224.8 | 699.1 | 489.6 | 820.4 |
| Minimum Dosage (mJ/cm$^2$) | 7.037 | 11.41 | 12.42 | 11.63 |
| Standard Deviation (mJ/cm$^2$) | 17.23 | 29.18 | 24.15 | 25.24 |

As illustrated in Table 3, the highest mean UV dosage (e.g., 33.42 mJ/cm$^2$) occurs with a length of approximately 185.0 mm. Furthermore, highest maximum dosage of UV occurs at a length of 370.0 mm, with approximately 820.4 mJ/cm$^2$, and the lowest minimum UV dosage occurs at a length of 92.50 mm, with approximately 7.037 mJ/cm$^2$. The highest standard deviation occurs at a length of 185.0 mm, with a standard deviation of 29.18.

Alternative factors may additionally affect the UV dosage within the flow cell 10. With reference to Table 4 below, altering the shape of the flow cell 10 while maintaining a constant flow rate (2 L/min) impacts the UV dosage within the flow cell 10. Specifically, the results below were collected from a cylindrical flow cell and a conical flow cell, each including two 30 mW UV LEDs.

TABLE 4

Impact of Faucet Flow Cell Shape on UV Dosage and Pressure

| | Microbes D10 (mJ/cm$^2$/log) | | | | | | Mean Dosage (mJ/cm$^2$) | Pressure Drop (Pa) |
|---|---|---|---|---|---|---|---|---|
| | 1 | 5 | 10 | 20 | 40 | 80 | | |
| Cylindrical Faucet Flow Cell | 4.95 | 7.26 | 8.32 | 9.26 | 10.1 | 10.7 | 11.7 | 6,365.8 |
| Conical Faucet Flow Cell | 6.58 | 9.08 | 10.4 | 11.7 | 12.7 | 13.4 | 14.4 | 6,279.9 |

As illustrated in Table 4, the conical flow cell includes highest mean UV dosage (e.g., 14.4 mJ/cm$^2$), whereas the cylindrical flow cell includes a mean UV dosage of 11.7 mJ/cm$^2$. Alternatively, the cylindrical flow cell includes a greater pressure drop (e.g., 6,365.8 Pa) than the conical flow cell (e.g., 6,279.9 Pa).

With reference to Table 5 below, altering the shape and reflectivity of the flow cell 10 while maintaining a constant flow rate (2 L/min) impacts the UV dosage within the flow cell 10. Specifically, the results below were collected from a cylindrical flow cell and a conical flow cell, each including two 30 mW UV LEDs. Additionally, both the cylindrical and conical flow cell include a reflective element positioned on an end wall.

TABLE 5

Impact of Faucet Flow Cell Shape and End Reflective Element on UV Dosage and Pressure

| Microbes D10 (mJ/cm$^2$/log) | 1 | 5 | 10 | 20 | 40 | 80 | Mean Dosage (mJ/cm$^2$) | Pressure Drop (Pa) |
|---|---|---|---|---|---|---|---|---|
| Cylindrical Faucet Flow Cell | 8.75 | 12.5 | 14.6 | 16.8 | 18.7 | 20.4 | 24.8 | 6,365.8 |
| Conical Faucet Flow Cell | 8.34 | 11.4 | 13.2 | 14.9 | 16.3 | 17.4 | 19.1 | 6,279.9 |

As illustrated in Table 5, the cylindrical flow cell includes highest mean UV dosage (24.8 mJ/cm$^2$), whereas the conical flow cell includes a mean UV dosage of 19.1 mJ/cm$^2$. Alternatively, the cylindrical flow cell includes a greater pressure drop (e.g., 6,365.8 Pa) than the conical flow cell (e.g., 6,279.9 Pa).

With reference to Table 6 below, altering the outlet jet angle $\theta_b$ while maintaining a constant flow rate (2 L/min) impacts the UV dosage within the flow cell 10. Specifically, the results below were collected from a cylindrical flow cell including two 30 mW UV LEDs.

TABLE 6

Impact of Outlet Jet Angle on UV Dosage and UV Intensity

| Microbes D10 (mJ/cm$^2$/log) | 1 | 5 | 10 | 20 | 40 | 80 | Mean Dosage (mJ/cm$^2$) | Outlet UV Intensity (W/m$^2$) |
|---|---|---|---|---|---|---|---|---|
| Outlet Jet Angle 0° | 8.75 | 12.5 | 14.6 | 16.8 | 18.7 | 20.4 | 24.8 | 4.56 |
| Outlet Jet Angle 10° | 8.77 | 12.4 | 14.6 | 16.8 | 18.7 | 20.3 | 23.1 | 5.11 |
| Outlet Jet Angle 45° | 9.02 | 12.7 | 14.8 | 16.8 | 18.5 | 19.8 | 22.2 | 7.92 |

As illustrated in Table 6, the highest mean UV dosage (e.g., 24.8 mJ/cm$^2$) occurs with the 0° outlet jet angle $\theta_b$, and the lowest mean UV dosage (e.g., 22.2 mJ/cm$^2$) occurs with the 45° outlet jet angle $\theta_b$. Alternatively, the highest outlet UV intensity (e.g., 7.92 W/m$^2$) occurs with the 45° outlet jet angle $\theta_b$, and the lowest outlet UV intensity (e.g., 4.56 W/m$^2$) occurs with the 0° outlet jet angle $\theta_b$.

Operation of the faucet flow cell 10 is initiated when a user opens a faucet communicating (i.e., downstream of) with the outlet 18. The faucet may include, for example, an actuator (e.g., a handle). When the actuator is actuated, water starts to flow through faucet flow cell 10 and the UV LEDs 40 are automatically turned on. Specifically, the UV LEDs 40 may turn off as soon as the faucet 10 is closed. Alternatively, the UV LEDs 40 may remain on for a predetermined time period (e.g., 1-30 seconds) after the faucet is closed and water flow ceases, in order to disinfect residual water within the flow cell 10. Furthermore, the UV LEDs 40 may be periodically turned on when the faucet flow cell 10 is off in order to disinfect stagnant, residual water within the flow cell 10. In some embodiments, only one of the UV LEDs 40 may be turned on. In further alternative embodiments, a UV LED may be positioned in the outlet 18 of the flow cell 10 in order to irradiate water as it is exiting the flow cell 10.

In alternative embodiments, one or more sensors may be placed on the sidewall 22 and/or end walls 26a, 26b of the flow cell 10. The sensors are operable to detect LED optical output, which is proportional to operating current. As UV intensity drops (e.g., the UV LEDs 40 dim and/or turn off), the sensors will sense the reduction, and communicate with a circuit board. The circuit board will subsequently increase an operating current in order to offset the output loss from the UV LEDs 40.

In still further embodiments, current may be adjusted periodically throughout operation in order to maintain a predetermined intensity value. More specifically, the UV LEDs 40 may be operated at a lower current, thereby extending the operating life of the UV LEDs 40. A timer may additionally be installed into the faucet flow cell 10 to track operating time. Specifically, the timer may be in communication with the circuit board, allowing the circuit board to adjust the current after a predetermined amount of time (e.g., every 100-1,000 hours).

In still further embodiments, a thermo-management device (e.g., a cooling fan, a thermoelectric cooler (TEC), etc.) may be installed in the faucet flow cell 10. Specifically, the thermo-management device may be used in the back of the UV LEDs 40, replacing a traditional heat sink. The thermo-management device may be in connection with the circuit board and the sensor and/or the timer to predict the optical power of the UV LEDs 40. The thermo-management device may then be turned "ON" when the optical power of the UV LED 40 drops below a LED junction temperature.

Various features and advantages of the disclosure are set forth in the following claims.

What is claimed is:

1. A water dispensing unit adapted for communication with a water supply, the water dispensing unit comprising:
a main body including a first end, a second end opposite the first end, a first axis extending through the first and second ends, and a second axis extending perpendicular to the first axis;
an inlet configured to receive water from the water supply;
an outlet configured to dispense water, wherein the outlet extends along an outlet axis;
an inner wall including a reflective liner; and
a light emitting diode positioned within the main body;
wherein the outlet axis is oriented at an angle relative to the second axis to direct water from the water supply toward the light emitting diode before exiting through the outlet;
wherein the outlet axis is oriented within a range of 10-45 degrees relative to the second axis.

2. The water dispensing unit of claim 1, wherein the inlet extends along an inlet axis, and wherein the inlet axis is oriented at an angle relative to the second axis to direct water toward the light emitting diode.

3. The water dispensing unit of claim 2, wherein the inlet axis is oriented within a range of 5-20 degrees relative to the second axis.

4. The water dispensing unit of claim 1, wherein the light emitting diode forms a zone including a UV intensity level greater than a UV intensity level of the remainder of the main body.

5. The water dispensing unit of claim 4, wherein the zone is configured to irradiate water from the water supply when the water flows through the zone.

6. The water dispensing unit of claim 4, wherein the outlet axis is oriented to direct water into the zone prior to flowing through the outlet.

7. A water dispensing unit adapted for communication with a water supply, the water dispensing unit comprising:
a main body including a first end, a second end opposite the first end, and a longitudinal axis extending through the first and second ends;
an inlet configured to receive water from the water supply;
an outlet configured to dispense water;
a liner positioned along an inner surface of the main body, wherein the liner includes a first reflectivity value; and
an end wall positioned on the first end of the main body, wherein the end wall includes a light window and a light emitting diode, and wherein the end wall includes a second reflectivity value greater than the first reflectivity value.

8. The water dispensing unit of claim 7, wherein the liner, the light emitting diode, and the light window are operable to disinfect water from the water supply.

9. The water dispensing unit of claim 7, further comprising a second end wall positioned on the second end of the main body.

10. The water dispensing unit of claim 9, wherein the second end wall includes a third reflectivity value less than or equal to the second reflectivity value.

11. The water dispensing unit of claim 9, wherein the second end wall includes a second light window and a second light emitting diode.

12. The water dispensing unit of claim 7, wherein the end wall includes a second liner, wherein the liner includes a first thickness value, and the second liner includes a second thickness value, and wherein the second thickness value is greater than the first thickness value.

13. The water dispensing unit of claim 7, further comprising a sensor positioned within the main body, wherein the sensor is operable to detect an optical output of the light emitting diode.

14. The water dispensing unit of claim 7, wherein the light emitting diode is configured to emit light when water is flowing through the main body, and wherein the light emitting diode is configured to automatically turn off when water flows through the outlet.

15. The water dispensing unit of claim 7, wherein the light emitting diode is configured to emit light for a predetermined period of time after water flows through the outlet.

16. The water dispensing unit of claim 7, further comprising a cap positioned on one of the first end and the second end, wherein the cap includes a first length, and the main body includes a second length, and wherein the first length is less than the second length.

17. The water dispensing unit of claim 16, wherein the cap includes a fourth reflectivity value greater than the first reflectivity value.

18. A water dispensing unit adapted for communication with a water supply, the water dispensing unit comprising:
a main body including a first end, a second end opposite the first end, a first axis extending through the first and second ends, and a second axis extending perpendicular to the first axis;
an inlet configured to receive water from the water supply, wherein the inlet extends along an inlet axis;
an outlet configured to dispense water, wherein the outlet extends along an outlet axis;
a liner positioned along an inner surface of the main body, wherein the liner includes a first reflectivity value; and
an end wall positioned on one of the first end and the second end of the main body, wherein the end wall includes a light window and a light emitting diode, wherein the end wall includes a second reflectivity value greater than the first reflectivity value;
wherein one of the inlet axis and the outlet axis is oriented at an angle relative to the second axis to direct water from the water supply toward the light emitting diode.

19. The water dispensing unit of claim 18, wherein the light emitting diode forms a zone including a UV intensity level greater than a UV intensity level of the remainder of the main body.

* * * * *